United States Patent
Ouchi et al.

(10) Patent No.: US 7,542,140 B2
(45) Date of Patent: Jun. 2, 2009

(54) DETECTION METHOD USING ELECTROMAGNETIC WAVE AND DETECTION APPARATUS

(75) Inventors: Toshihiko Ouchi, Sagamihara (JP); Shintaro Kasai, Tokyo (JP); Haruko Yoneyama, Saitama (JP); Masatsugu Yamashita, Sendai (JP)

(73) Assignees: Canon Kabushiki Kaisha, Tokyo (JP); Riken, Saitama-Ken (JP)

( * ) Notice: Subject to any disclaimer, the term of this patent is extended or adjusted under 35 U.S.C. 154(b) by 0 days.

(21) Appl. No.: 11/948,466

(22) Filed: Nov. 30, 2007

(65) Prior Publication Data

US 2008/0137068 A1    Jun. 12, 2008

(30) Foreign Application Priority Data

Dec. 5, 2006    (JP)    ............................. 2006-327801

(51) Int. Cl.
    *G01B 11/00*    (2006.01)
(52) U.S. Cl. ........................ 356/394; 356/388; 356/316
(58) Field of Classification Search ................. 356/394, 356/300, 316
    See application file for complete search history.

(56) References Cited

U.S. PATENT DOCUMENTS

| | | | |
|---|---|---|---|
| 6,332,087 B1 * | 12/2001 | Svenson et al. .............. 600/407 |
| 6,500,618 B1 | 12/2002 | Woolard et al. ................. 435/6 |
| 2003/0226969 A1 | 12/2003 | Williamson ............... 250/341.1 |
| 2004/0058339 A1 | 3/2004 | Nagel et al. ..................... 435/6 |
| 2006/0029941 A1 | 2/2006 | Koo et al. ....................... 435/6 |
| 2006/0217612 A1 | 9/2006 | Ouchi ......................... 600/407 |
| 2007/0279136 A1 | 12/2007 | Koyama et al. .......... 331/107 T |

FOREIGN PATENT DOCUMENTS

| | | |
|---|---|---|
| EP | 1630542 | 3/2006 |
| JP | 2005-172775 A | 6/2005 |

OTHER PUBLICATIONS

Engvall, E., et al., "Enzyme-linked immunosorbent assay (ELISA) Quantitative assay of immunoglobulin G", Immunochemistry, vol. 8, No. 7, pp. 871-874 (1971).

(Continued)

*Primary Examiner*—Roy Punnoose
(74) *Attorney, Agent, or Firm*—Fitzpatrick, Cella, Harper & Scinto

(57) ABSTRACT

A detection apparatus includes a sample holding section, an irradiation means, a detection means, a calculation means, and an evaluation means. The irradiation means irradiates a substance held in the sample holding section with a THz wave. The detection unit detects a THz wave that has passed through or been reflected from the substance. The calculation unit determines a frequency dependence of a property of the substance with respect to the irradiated THz wave and then calculates a slope of a straight line or a slope of a straight line obtained by straight-line approximation of the frequency dependence of the property of the substance. The evaluation unit evaluates the state change of the substance by comparing a previously-obtained slope of a straight line of the frequency dependence of the property of the substance in a standard state and the slope of the straight line of the substance calculated.

12 Claims, 17 Drawing Sheets

OTHER PUBLICATIONS

W. Neal Burnette, "'Western Blotting': Electrophoretic Transfer of Proteins from Sodium Dodecyl Sulfate-Polyacrylamide Gels to Unmodified Nitrocellulose and Radiographic Detection with Antibody and Radioiodinated Protein A", Analytical Biochemistry, vol. 112, pp. 195-203 (1981).

J Knab et al., "Critical Hydration and Temperature Effects on Terahertz Biomolecular Sensing", *Proc. of SPIE*, 5995, 599505 (2005).

T Ouchi et al., "Terahertz Integrated Transmission Line Sensors Using a Bonded Epitaxial GaAs Layer on Silicon Substrates", *IEEE Transmission Lines and Antennas*, p. 273 (2006).

AG Markelz et al., "Pulsed Terahertz Spectroscopy of DNA, Bovine Serum Albumin and Collagen Between 0.1 and 2.0 THz", *Chemical Physics Letters*, 320 (2000) pp. 42-48 (Mar. 31, 2000).

H Yoneyama et al., "Application of a Membrane Device for Biosensing with Terahertz Time Domain Spectroscopy", *IEEE Biological and Medical Applications*, p. 506 (2006).

\* cited by examiner

DETECTION METHOD USING ELECTROMAGNETIC WAVE AND DETECTION APPARATUS

BACKGROUND OF THE INVENTION

1. Field of the Invention

The present invention relates to a technology with respect to a detection method and a detection apparatus for obtaining information about a substance (sample) using an electromagnetic wave (referred to as a "terahertz wave", or "THz wave", herein) selected from a frequency range of 0.1 THz to 10 THz.

2. Description of the Related Art

In recent years, technologies using THz waves have actively progressed. In particular, the photon energies of THz waves are almost the same in level as those of skeletal vibrations of molecules and molecular interactions. Thus, spectra obtained by spectroscopic technologies have been used for the analysis of substances.

For such technologies, Japanese Patent Application Laid-Open No. 2005-172775 discloses a detection method for identifying a substance in a food product by irradiating THz waves having frequencies equal to characteristic vibration frequencies corresponding to the structures of constituting elements of food products including DNAs, proteins, bacteria, and viruses. The above patent document describes that differences among them with respect to their structures, the presence or absence of denaturation, the presence or absence of toxins, and the like can be quickly and simply determined.

Since the THz waves have vibration frequencies specific to respective substances, thus, it is generally known that the presence of any substance and its state can be recognized from the spectrum information of the THz waves.

However, polymeric materials and hydrates include many materials that present difficulties in discrimination of characteristic vibration spectra in the THz wave region. Thus, the above method has not always been capable of identifying substances, for the following reason: polymers have an infinite number of characteristic frequencies at the frequency band of THz waves, so, as a result of superposition, it is difficult to separate and observe a characteristic peak. In addition, the characteristic frequencies resulting from intermolecular forces may disappear as the molecules may enter an amorphous, solution, or hydrated state. In this case, a conventional method, such as infrared spectroscopy, can be used. Known types of infrared spectroscopy includes Fourier transform infrared spectroscopy (FT-IR) and Raman spectroscopy. Spectrum data with respect to the binding of molecules with energy higher than THz waves has been stored in a database, so any substance can be simply evaluated.

In the case of protein analysis, for example, the ELISA method (*Immunochemistry*, vol. 8, pp. 871-874, Pergamon Press, 1971) and the Western Blotting method (*Analytical Biochemistry*, vol. 112, pp. 195-203, 1981) have been known as methods using antigen-antibody reactions. Those methods permit high-sensitivity measurements. Further, other methods using electromagnetic waves such as X-rays and light, magnetism, and ultrasonic waves are known for observing a state change inside a substance and a denatured state as a broad sense by measuring the crystal structure, phase transition phenomenon, phonon, collision relaxation phenomenon, and the like.

SUMMARY OF THE INVENTION

As described above, conventionally, there has been proposed no method for effective detection with THz waves when substances cannot be discriminated from one another with vibration spectrum specific to the THz wave band (about 0.1 to 10 THz). For example, in the case where the variation width of the frequency dependence of transmission spectrum is not sufficient in size with respect to the fluctuation of the base line of noises, a substance of interest cannot be identified. In addition, in the case where a phase-shift spectrum measured using terahertz time-domain spectroscopy (THz-TDS) shows only a linear variation, and therefore a distinct inflexion point, a distinct extreme point, and a distinct discontinuity are hardly detected, a substance of interest cannot be identified.

On the other hand, among the conventionally-used infrared spectroscopic methods, some vibration spectra are observed in FT-IR. However, they do not include an energy region for skeletal vibrations and intermolecular interactions specific to polymers in terms of energy. Thus, FT-IR has problems in that there is a limit in identification of a substance and there is a difficulty in quantitative analysis. In addition, it requires storing a sample in a vacuum chamber. Thus, it is difficult to measure a sample in a liquid or hydrate state in which biomolecules may function. In addition, the Raman spectroscopy has a problem of damaging soft materials because it observes a shift amount of a wavelength by excitation with high-energy laser rays. Further, because a Raman spectrum in the THz region is close to an excitation wavelength, it is difficult to distinguish the excitation wavelength from the Raman spectrum, resulting in a problem in accuracy.

Biochemical techniques such as the ELISA method, the Western Blotting method, and the like are extremely sensitive to certain molecules. However, those techniques are ones estimating from a difference in amino acid sequences of parts of the proteins after breaking the complete structures thereof into polypeptides. Therefore, there is a problem in diagnostic accuracy. This is because protein does not always function normally in this state, even if the investigator knows the correct sequence. Therefore, a technique for directly evaluating a three-dimensional higher-order structure (conformation) has been demanded.

The present invention has been made in view of the above-mentioned problems. The present invention provides a method of detecting a state change of a substance using an electromagnetic wave selected from a frequency range of 0.1 THz to 10 THz comprising the following first to fifth steps. In the first step, a substance is placed on a sample holding section. In the second step, the substance is irradiated with the electromagnetic wave. In the third step, an electromagnetic wave passed through or reflected from the substance is detected. In the fourth step, a frequency dependence of a property of the substance with respect to the irradiating electromagnetic wave from information about the detected electromagnetic wave and the irradiating electromagnetic wave is determined and then a slope of a straight line or a slope of a straight line obtained by straight-line approximation of the frequency dependence of the property of the substance is calculated. In the fifth step, the state change of the substance is evaluated by comparing a previously-obtained slope of a straight line of the frequency dependence of the property of the substance in a standard state and the slope of the straight line of the substance calculated. The frequency dependence of the property of the substance may be at least one selected from transmittance, absorbance, reflectance, and phase shift. In particular, the frequency range for determining the slope of the straight line of the frequency dependence of the property of the substance may be selected from a range of 0.2 THz to 2.5 THz.

Further, in consideration of the above-mentioned problems, the present invention provides an apparatus for detecting a state change of a substance using an electromagnetic wave selected from a frequency range of 0.1 THz to 10 THz comprising a sample holding section for holding a substance, an irradiation means, a detection means, a calculation means, and an evaluation means. The irradiation means irradiates the substance held in the sample holding section with the electromagnetic wave. The detection means detects an electromagnetic wave passed through or reflected from the substance. The calculation means determines a frequency dependence of a property of the substance with respect to the irradiating electromagnetic wave from information about the detected electromagnetic wave and the irradiating electromagnetic wave and calculates a slope of a straight line or a slope of a straight line obtained by straight-line approximation of the frequency dependence of the property of the substance. The evaluation means evaluates the state change of the substance by comparing a previously-obtained slope of a straight line of the frequency dependence of the property of the substance in a standard state and the slope of the straight line of the substance calculated by the calculation means.

According to the present invention, irrespective of the possibility of observation of characteristic vibration spectrum at the frequency band of a THz wave, the state change of a substance can be detected using the THz wave in a noncontact, nondestructive, and label-free manner. In this way, inspection efficiencies in pathological diagnoses for medical purposes, development/in-process inspection for industrial materials, and the like can be improved.

Further features of the present invention will become apparent from the following description of exemplary embodiments with reference to the attached drawings.

DESCRIPTION OF THE EMBODIMENTS

Figure 1:
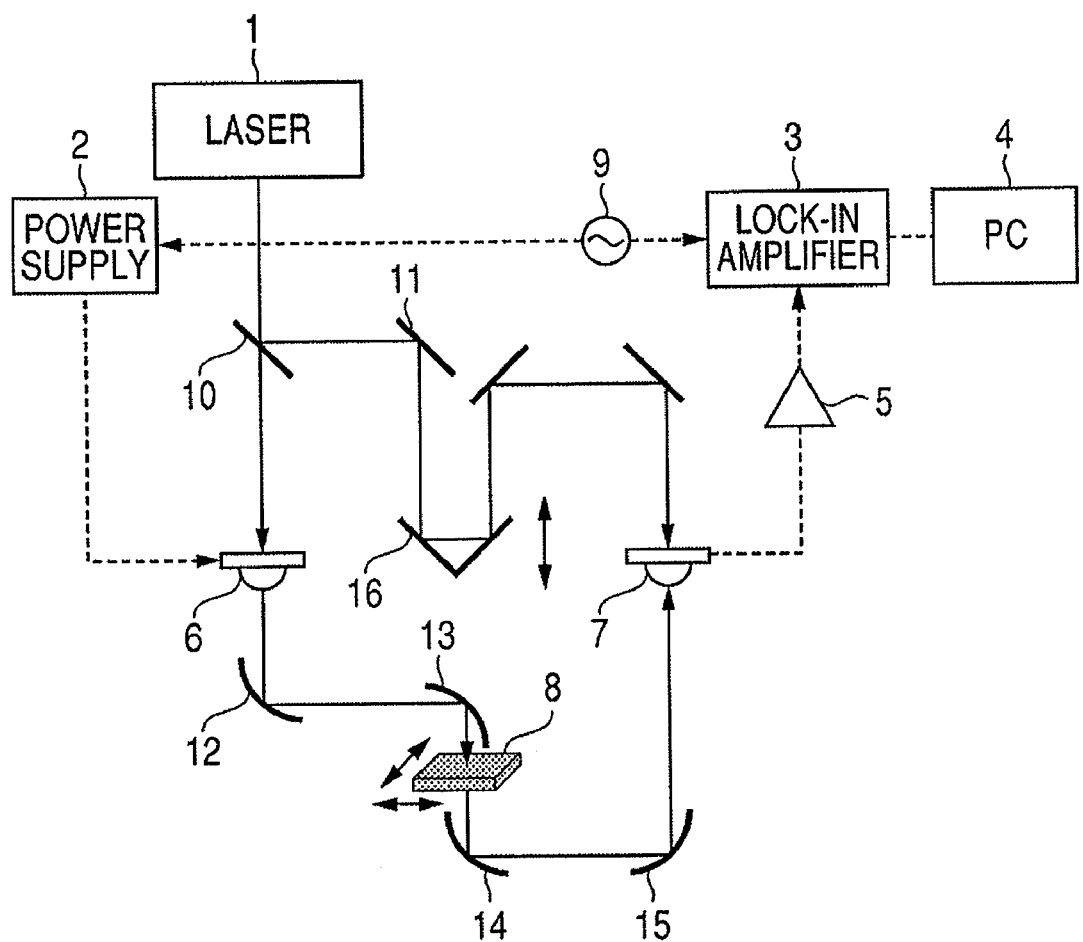
FIG. 1 is a block diagram illustrating a detection apparatus in accordance with embodiments of the present invention.

Hereinafter, a detection method and a detection apparatus according to the present invention will be described with reference to the preferred embodiments. The present invention is provided for detecting a state change of a substance. Typically, the detection is carried out on the degree of denaturation due to a structural change of a substrate from a normal state. In this case, the term "degree of denaturation" to be detected on a sample of a target is defined as the degree of denaturation state in which the whole or partial structure of the substrate is changed by a minor increase or decrease in elements, a change in binding state in component elements, and the like without a substantial change in major component elements of the substrate.

As for bio-related molecules such as proteins, nucleic acids (e.g., DNA), and sugars, for example, the whole conformation (as for DNA, including difference between a single strand and a double strand) changes when binding state changes. Such a change may be caused by, for example, heating or light irradiation. This is very important in application because, in the human body, the denatured molecule present due to an occurrence of a certain abnormality or a congenital origin leads to the expression, diagnosis, or the like of a disease. For instance, diseases such as cancer, BSE (mad cow disease), melanoma, and amyotrophic lateral sclerosis (ALS) have been known to be expressed when certain denatured proteins are present. Thus, it is important to examine those proteins by a simple method.

The detection method and the detection apparatus of the present invention are applicable to the detection of a state change in industrially-important constituent material. Examples of organic materials include organic luminescent materials, organic semiconductors, dyes, pigments, colorants, and toners. The detection method and the detection apparatus of the present invention may be applied to the detection of the state of expression/degradation due to the structural change, the detection of a doping state, the detection of color, and the like of those materials. On the other hand, similarly, the detection method and the detection apparatus of the present invention may be applicable to inorganic materials such as luminescent materials, semiconductors, dielectric materials, liquid crystals, dyes, pigments, colorants, and toners in order to detect the state change thereof. The detection method and the detection apparatus of the present invention can be applied to check examination in the material development process, manufacturing process, and the like.

In this case, an embodiment in which the detection method and the detection apparatus of the present invention is applied to a protein assay will be described. In this embodiment, an appropriate apparatus is used depending on the particular substance that is of interest. However, the detection method and detection apparatus for detecting a state change of a substance at the THz wave band of 0.1 to 10 THz are common to various substances.

First, an embodiment of the detection apparatus using THz waves will be described with reference to FIG. 1. This apparatus uses THz wave pulses with pulse widths of a picosecond or less, which can be generated by irradiating a semiconductor material with a femtosecond laser.

In the configuration of the apparatus of FIG. 1, a laser beam with a wavelength of 780 nm and an average power of 40 mW emitted from a fiber-type femtosecond laser 1 with a pulse width of 100 fsec is divided into two paths by a half mirror 10. One path irradiates the light onto a photoconductive device 6 on the electromagnetic-wave generating side. Another path irradiates the light onto a photoconductive device 7 on the receiving side through a time delay stage 16 using a plurality of mirrors 11 (one having the same function is not numbered). The photoconductive devices 6 and 7 may be those commonly used, each formed with a dipole antenna having an interval portion in LT-GaAs. However, the photoconductive devices 6 and 7 are not particularly limited to such devices. As far as a laser beam used has a narrower pulse width of 10 fsec, the band for dispersion of light with THz waves can be extended. In addition to a fiber laser, a solid-state laser such as titanium sapphire may be used. Further, for the generation and detection of a THz wave, the semiconductor surface may be used without an antenna. Alternatively, an electro-optic crystal such as a ZnTe crystal may be used. In this case, a power supply 2 may apply a suitable bias voltage on the interval portion of the photoconductive device 6 on the electromagnetic-wave generating side.

The THz wave thus generated is made into a collimated beam by a paraboloidal mirror 12 and then irradiated on a sample (test substance) 8 held by a sample holding section by a paraboloidal mirror 13. In this embodiment, the irradiation unit includes a fiber-type femtosecond laser 1 and the photoconductor device 6.

The THz wave passed through the sample 8 is received again by the photoconductive device 7 through paraboloidal mirrors 14 and 15. In this embodiment, the detection unit includes the fiber-type femtosecond laser 1, the time delay stage 16, and the photoconductive device 7.

At this time, for allowing the sample 8 to be measured at a plurality of places, the sample 8 may be movable in a fixed plane. The THz wave signal received by photoconductive device 7 is amplified with amplifier 5, and then acquired as a time waveform by a lock-in amplifier 3. After carrying out signal processing such as Fourier transform by means of a personal computer (PC) 4 containing a calculation unit, a transmission spectrum, a phase shift spectrum, and the like of the sample 8 can be calculated. For acquiring a THz wave signal with the lock-in amplifier 3, a signal from an oscillator 9 modulates (amplitude 5V to 30V) a bias voltage to be applied from the power supply 2 to the interval of the photoconductive device 6 on the generating side by a signal from an oscillator 9 is modulated. As a result, an S/N ratio can be improved by carrying out a synchronous detection. The detection method as described above is generally referred to as terahertz time-domain spectroscopy (THz-TDS).

Figure 2:
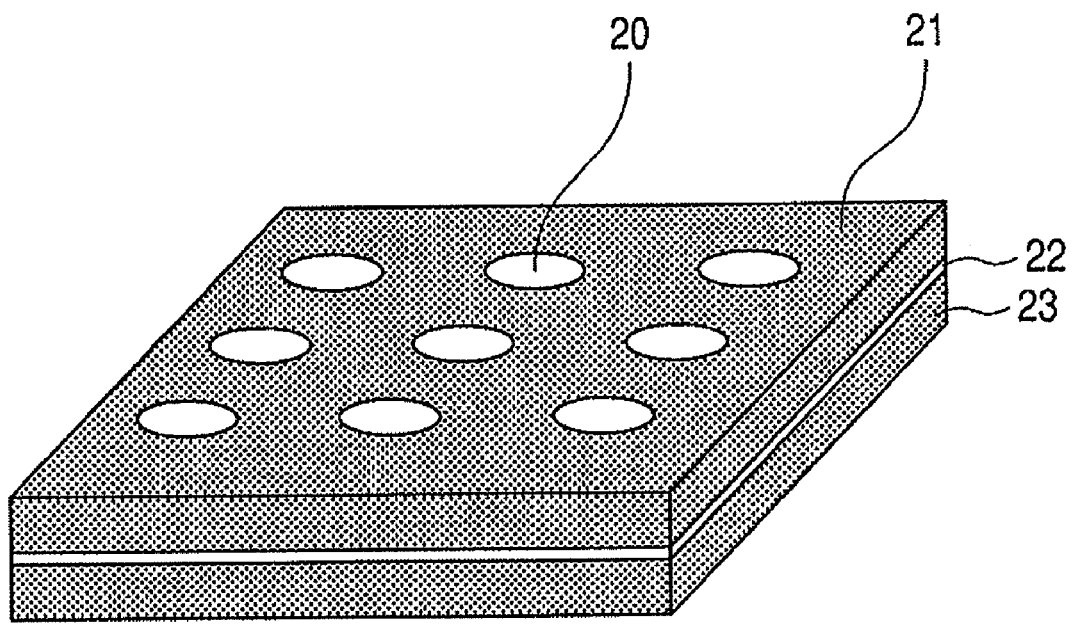
FIG. 2 is a perspective view illustrating an example of a sample holding member to be used in the detection apparatus.

The sample 8 may be directly placed on the position of the holding section if the sample 8 is of a solid form. In contrast, if the substance is of a liquid form, it may be impregnated in a micromembrane filter (e.g., Supor™ manufactured by Nihon Pall Ltd.) or the like and then assayed. A member for holding the sample in such a case is illustrated in FIG. 2. The sample is injected into a partition (well) 20 for preventing samples from interfering with each other and then fixed on a micromembrane filter 22. In FIG. 2, the reference numeral 21 denotes a member made of a resin or the like and forming a well 21. The reference numeral 23 denotes a metal member used for blocking the stray light or noise light of THz wave light. The micromembrane filter 22 is sandwiched between the member 21 and the metal member 23.

Figure 3A:
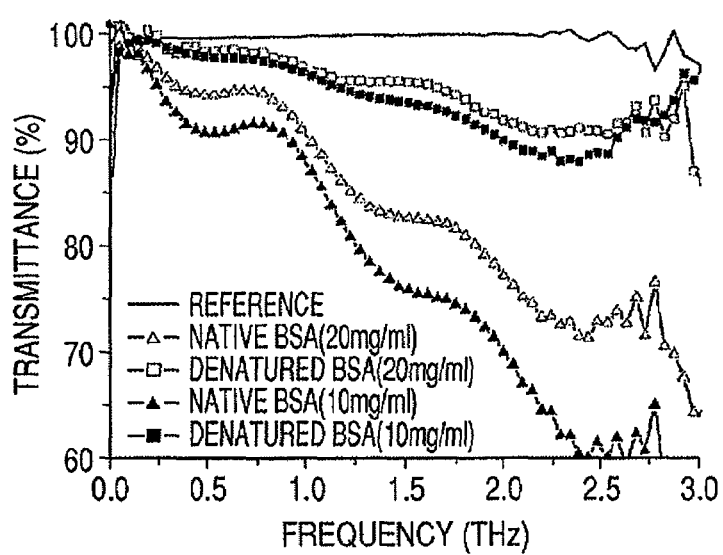
FIGS. 3A, 3B and 3C are graphic diagrams illustrating examples of a transmission spectrum, a phase shift spectrum, and a time waveform of protein (BSA).
Figure 3B:
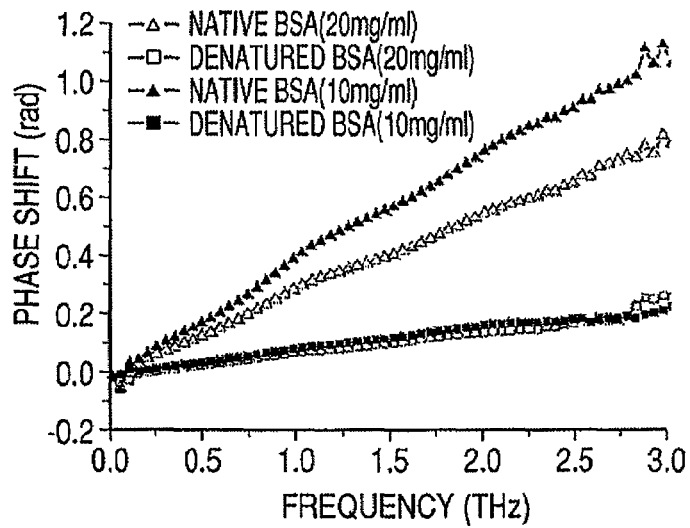
Figure 3C:
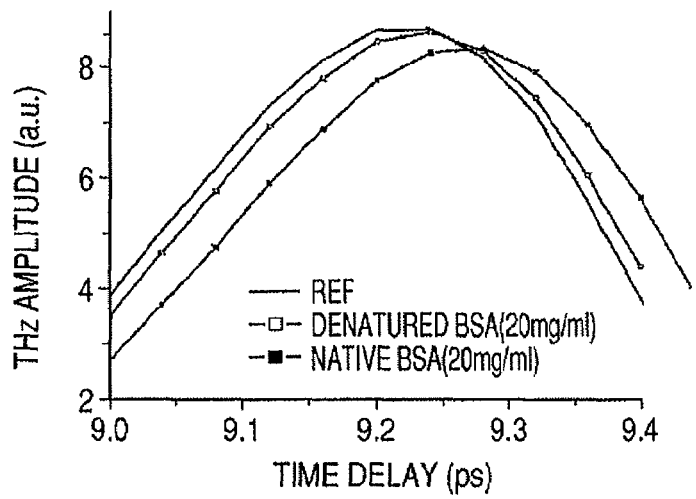

In this way, a THz wave absorption spectrum of bovine serum albumin (BSA), which is a protein, was investigated. As a result, frequency dependences ((a) transmission spectrum, (b) phase shift spectrum, and (c) time waveform) different depending on the amount of protein and the denaturated state were obtained as illustrated in FIGS. 3A to 3C. In FIGS. 3A and 3B, the solid line indicates a result of the reference state free of the sample in holding member. The white-triangle line indicates a result of calculating the difference obtained by subtracting one obtained by immersing the sample in normal state at a concentration of 20 mg/ml from one in reference sate. The white-square line indicates a result of calculating the difference obtained by subtracting one obtained by immersing the sample in denatured state at a concentration of 20 mg/ml from one in reference state. The black-triangle line indicates a result of calculating the difference obtained by subtracting one obtained by immersing the sample in normal state at a concentration of 10 mg/ml from one in reference. The black-square line indicates a result of calculating the difference obtained by subtracting one obtained by immersing the sample in denatured state at a concentration of 10 mg/ml from one in reference sate. In FIG. 3C, the solid line indicates a result of the reference state in which the holding member is free of the sample. The white-circle line indicates a result of calculating the difference by subtracting one obtained by immersing the sample in denatured state at a concentration of 20 mg/ml from one in reference sate. The black-circle line indicates a result of calculating the difference by subtracting one obtained by immersing the sample in normal state at a concentration of 20 mg/ml from one in reference state.

The characteristic vibration spectrum cannot be determined as is evident from the transmission spectra in FIG. 3A with respect to the measurement conditions and the state of the sample. However, it is found that a notable difference in transmission spectra can be observed. This will also be described in the examples described later. In FIG. 3A, a wave undulation observed in the curve of the graph is caused as a result of interference between the upper and bottom surfaces of the micromembrane filter 22 and is irrelevant to a characteristic vibration spectrum. In this case, in particular, a large difference between the denatured sate and the normal state can be observed by comparing the slopes of the respective lines with line approximation at a range of 0.2 to 2.5 THz. Similarly, further, the phase shift spectra in FIG. 3B and the time wave shifts in FIG. 3C can be compared, respectively, and are useful in detection of the denatured state. It should be noted that the transmission spectra in FIG. 3A and the phase shift spectra in FIG. 3B are obtained by performing the process such as Fourier transform on the time waveform of FIG. 3C, which is raw data measured by THz-TDS.

In this embodiment, for a substance in reference state with respect to at least one of an appropriate concentration and the total number of moles, the above characteristics were stored as calibration curves in data base. Subsequently, the ratio (slope) of change with respect to their respective frequencies was compared with the ratio (slope) of change with respect to the actual frequency of the measurement sample calculated by the calculated unit PC4, thereby evaluating the degree of the denatured substance being mixed in the measurement sample by the evaluation unit of the above PC 4.

In this case, the transmittance measurement has been described as an example. Alternatively, the absorbance (calculated from the transmittance) may be calculated or the reflectance measurement (performed by detecting a reflected wave from the sample) may be carried out. Further, needless to say, the result of absorpance measurement may be used instead of (or in combination with) the measurement of transmittance or absorbance. In addition, as another embodiment, there is a method employing a total reflection optical system as described in the example described later or a detection method using the propagation of THz wave in a transmission line.

Figure 9:
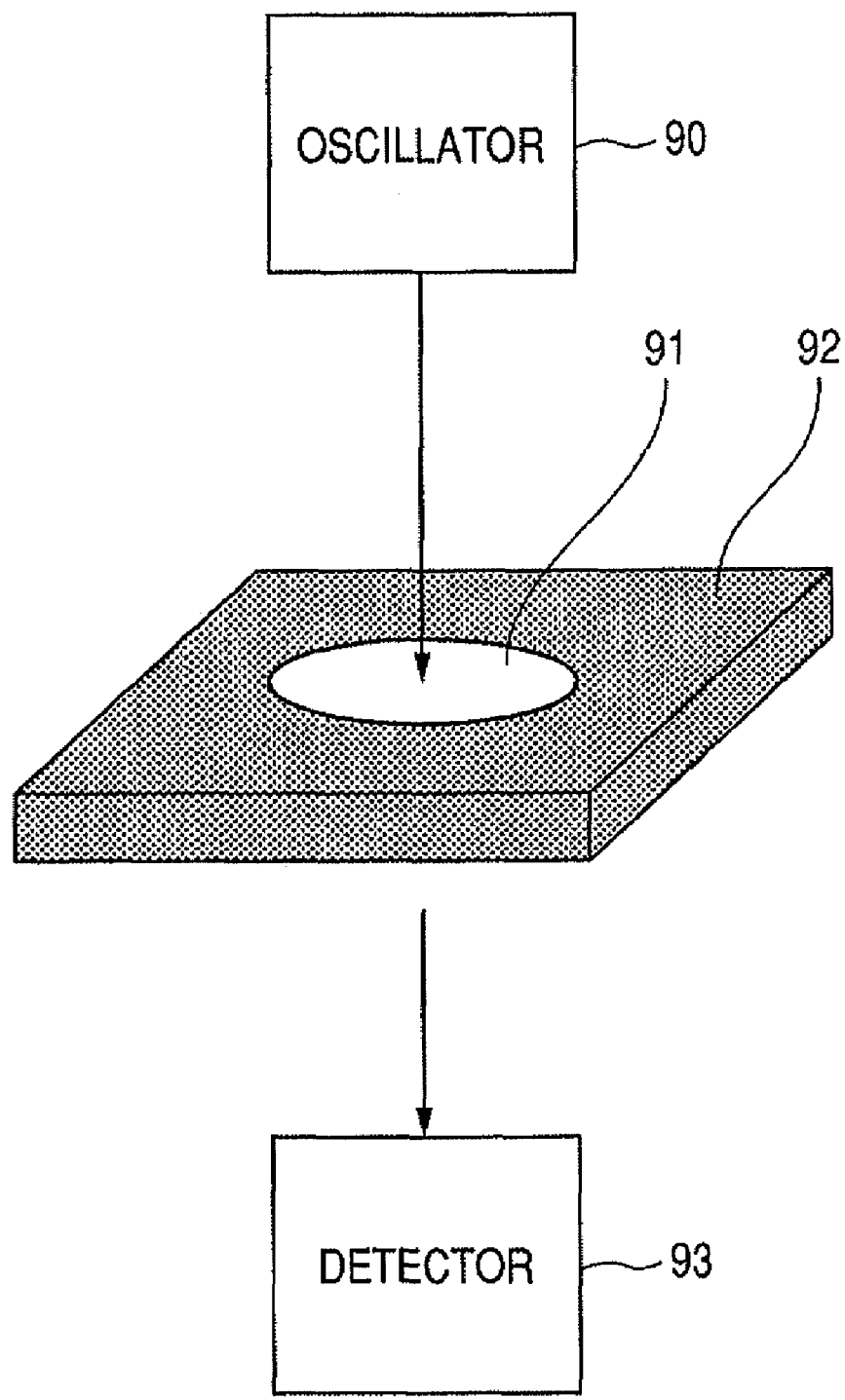
FIG. 9 is a block diagram illustrating a detection apparatus in accordance with another embodiment of the present invention.

Further, this embodiment has been described as an example using a unit in which a measurement is carried out with a THz wave pulse using THz-TDS. However, the detection may be performed by employing a plurality of THz wave optical sources with a single frequency such as a backward traveling wave oscillator, a quantum cascade laser, and a resonant tunneling diode, to calculate the ratio of changes as a slope from the transmittance, absorbance, reflectance, phase shift, or the like at the respective frequency points. An example of a measurement system is illustrated in FIG. 9. A THz wave generated from an oscillator 90 provided as an irradiation unit is irradiated on a sample 91 held in a holding member 92. The THz wave passed through the sample 91 is then detected by a detector 93, followed by calculating the transmittance of the sample 91.

Further, a wavelength-variable THz wave light source such as a parametric oscillator may be used to calculate the transmittance at a plurality of frequency points and then the above slope of the straight line may be calculated. Further, the Fourier transform infrared spectrophotometer (FT-IR) is able to obtain a transmission spectrum in a wide range of approximately 1 THz to several 100 THz. Therefore, the FT-IR may be effective in measurement at a frequency band, for example, 3 to 10 THz, which is an insufficient S/N ratio for THz measurement apparatus.

As can be seen from the above description, the detection method of the present invention is intended for an overall change in frequency spectrum. Thus, it can be applied to the case in which the characteristic vibration spectrum of a substance cannot be specified. In addition, the detection method does not detect a change in peak value even when the characteristic vibration spectrum is present. The detection method detects the slope when a discontinuity with a peak or monotonous curve portion without a turning point is approximated to a straight line, therefore, similarly, the detection method of the present invention can be applicable.

As described above, according to the present embodiment, the detection method and apparatus for detecting a state change of a substrate (e.g., degree of denaturation) with a THz wave can be realized by a simple measurement system.

EXAMPLES

Hereinafter, more specific examples will be described.

Example 1

Example 1 of the present invention will be described. In Example 1, the THz-TDS apparatus of FIG. 1 as described above was used and then the THz wave transmission spectra of both the normal and heat-denatured BSA protein were examined. This was carried out by dropping the BSA protein onto a membrane device prepared such that a micromembrane filter 22 was partitioned by the respective wells 20 as illustrated in FIG. 2. For the heat-denaturation conditions, the process was carried out at 72 to 75° C. for 3 minutes. In addition, the dropped samples were those obtained by dissolving normal and heat-denatured BSA protein samples in purified water such that concentrations thereof became 10 mg/ml and 20 mg/ml, respectively. Each of the former (10 mg/ml) was 60 µl and the latter (20 mg/ml) was supplied at a volume of 30 µl so that they could be equal to each other with respect to the number of moles, followed by being compared with each other.

As a result, as illustrated in FIG. 3A, the transmission spectrum of the protein at a frequency range of 0.2 THz to 3 THz showed a significant difference at any concentration when making a comparison between the normal BSA and the heat-denatured BSA. The "native" written in the graph represents the result of "normal," "denatured" represents the result of "denatured," and "reference" or "REF" represents the result of the case where only purified water used in the solution preparation was dropped.

Further, the peak positions of the THz-wave time waveform after passing through the membrane on which the denatured protein and the normal protein were dropped caused a time difference (see FIG. 3C). A phase shift spectrum with a reference showing the time difference was also illustrated in FIG. 3B. The phase shift spectrum shows a monotonically increasing, and it turns out that the slope thereof shows a significant difference depending on the presence or absence of denaturation and the concentration. In addition, even at any concentration, it is found that the denatured BSA shows a higher level of transmittance and a smaller rate of change of the phase shift compared with those of the normal BSA. In addition, an increase in transmittance and a decrease in amount of phase shift were observed along with an increase in concentration. When the normal BSA and the denatured BSA are mixed together, the transmission spectrum and the phase shift spectrum are observed to be located at intermediary positions, respectively.

In FIGS. 3A and 3B, fluctuations in properties are observed at 2.7 THz or more because of a decrease in S/N ratio. For increasing the measurement accuracy at this region, the power of the THz wave may be increased or the averaging procedure may be carried out more. In addition, wavinesses are observed in a wide range of about 1 THz in the whole transmission spectrum. This is an effect of the Fabry-Perot etalon on both end sides of the membrane device with a thickness of 140 µm. Therefore, the calculation of a slope is performed after correcting the wavinesses.

In this way, the degree of denaturation of protein such as BSA can be detected by comparing the transmittances of the THz waves as long as the concentration and the supply amount of the protein are obtained. As a detection method, when observing with transmittance, for example, a comparison may be made with the slope of a straight line being subjected to a first-order approximation with the least square method at a range of 0.2 THz to 2.5 THz where a significant change can be observed. In addition, when observing with phase shift spectrum, a comparison may be made with the slope of a straight line being linearly changed at the same range of 0.2 Hz to 2.5 Hz. Those frequency ranges may be suitably selected at any portion where a significant difference in slopes can be easily determined depending on the sample.

On the other hand, the FT-IR apparatus may be used when the frequency spectrum at a wide band is measured. It is difficult to obtain the phase characteristics as in the case of the THz-TDS method as described above, and the measurement takes much time. However, it may be an effective method to obtain data at a higher-frequency area.

Figure 14:
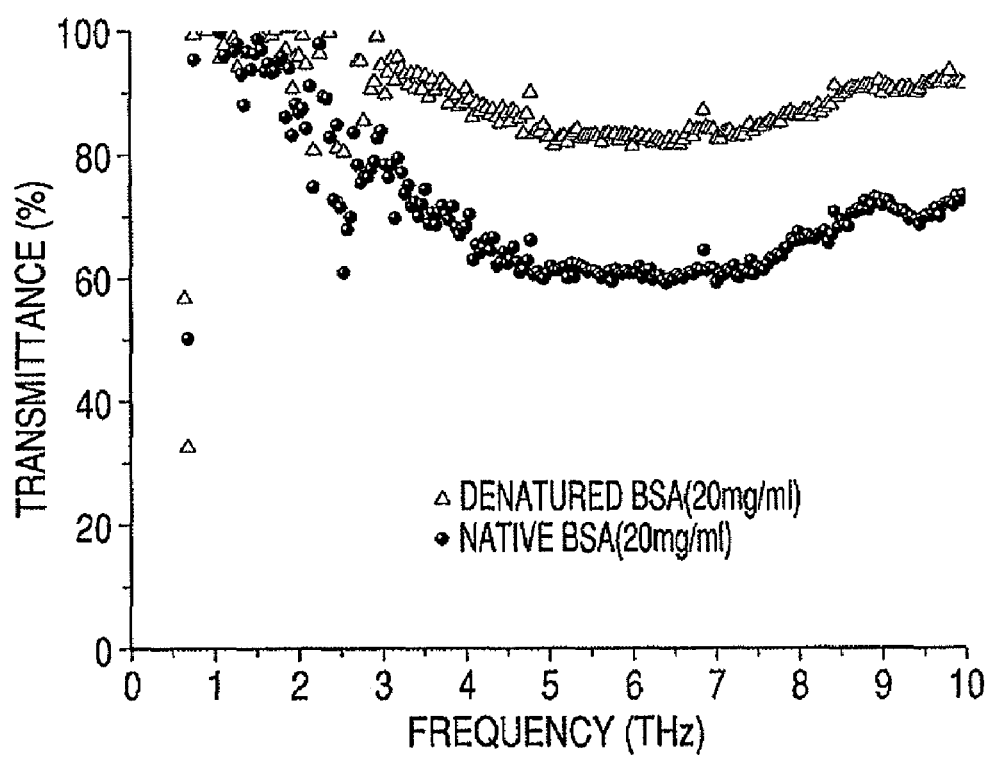
FIG. 14 is a graphic diagram illustrating another measurement example of the transmission spectrum of protein (BSA).

The results of measuring the same sample as one described above by the FT-IR apparatus are illustrated in FIG. 14. In FIG. 14, data obtained at 2 THz to 10 THz is illustrated. As in the case of THz-TDS, the denatured protein shows a higher transmittance than the normal one. For example, the properties are flat at 5 THz or more, so the distinction of normal/denatured can be performed by calculating and comparing the slopes of the straight-line approximated at 2 to 5 Hz.

It should be noted that in the FT-IR apparatus, S/N ratio at 3 THz or less becomes poor, which is a favorable range in the THz-TDS apparatus. Therefore, a mutual supplement may be performed if required.

A database of as many of calibration curves as possible are made and stored in a storage unit in advance as parameters including concentrations and the number of total supply amount of moles. Then, a ratio (slope) of the change with respect to the frequency of transmittance and the slope of the phase shift with respect to the frequency of the phase shift are compared to detect the degree of denaturation. All of these phenomena- transmission spectrum, phase shift spectrum, and time property- are associated with one another. Thus, the detection method may employ comparing transmission spectra or phase shift spectra, or judging from a combination of two or more thereof.

Figure 4A:
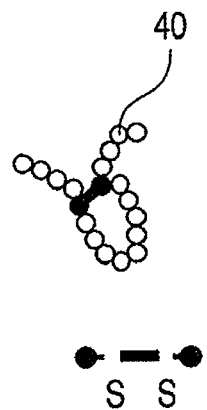
FIGS. 4A, 4B, 4C and 4D are diagrams illustrating a confirmation and the state change of the protein.
Figure 4B:
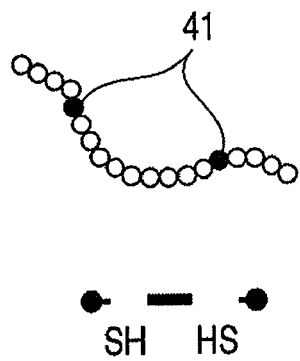
Figure 4C:
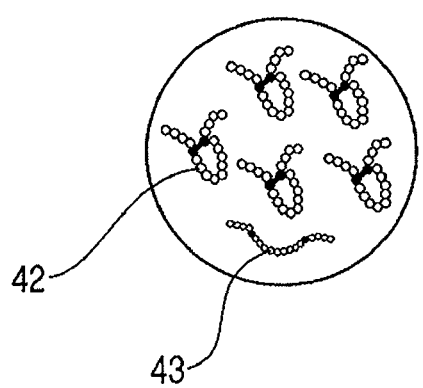
Figure 4D:
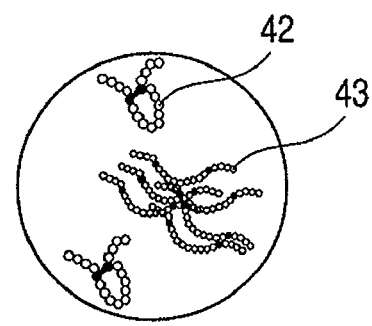

The reason of an increase in transmittance with heat denaturation as described above may be as follows: the conformational change of the heat-denatured protein may lead to the redistribution of energy between molecules, thereby causing changes in dielectric response between protein molecules and vibration mode in molecular population. Examples of the appearance of such influence are illustrated in FIGS. 4A to 4D. FIG. 4A illustrates protein in normal state. In this case, for example, the tertiary conformation of the protein is retained by the S—S bond 40 with sulfur. An entire appearance of such influence is illustrated in FIG. 4C. If the S—S bond is separated due to any cause, an S—H bond 41 is formed, thereby breaking the tertiary conformation of the protein. However, the S—H bond may be coupled again with an S—H bond of another molecule, so molecules may be coagulated with one another. FIG. 4D illustrates a denatured molecule 43 and a normal molecule 42, which are generated as mentioned above. As a result, between the state of FIG. 4C and the state of 4D, differences may occur in both the absorption coefficient and the reflective index with respect to the THz wave. It can also be explained from a difference in transmittance which occurs depending on the concentration even in normal state. In other words, if the concentration is low, the molecules may be uniformly dispersed and thus, the sectional area of the interaction with the THz wave may be increased, while the transmittance may be decreased. Whereas at high concentration, the molecules aggregate to some extent, and the higher the concentration increases, the higher the transmittance increases under the same number of moles. In fact, it may be expressed due to combination with other factors. This detection method can allow the observation of, in the case of a protein, not only a detection of abnormal protein due to denaturation but also a detection of a change in conformation of protein due to binding with a ligand molecule such as a vitamin or hormone, or due to binding between proteins. This method provides a simple determination of a protein structure and can be a useful tool in clinical use.

Figure 5:
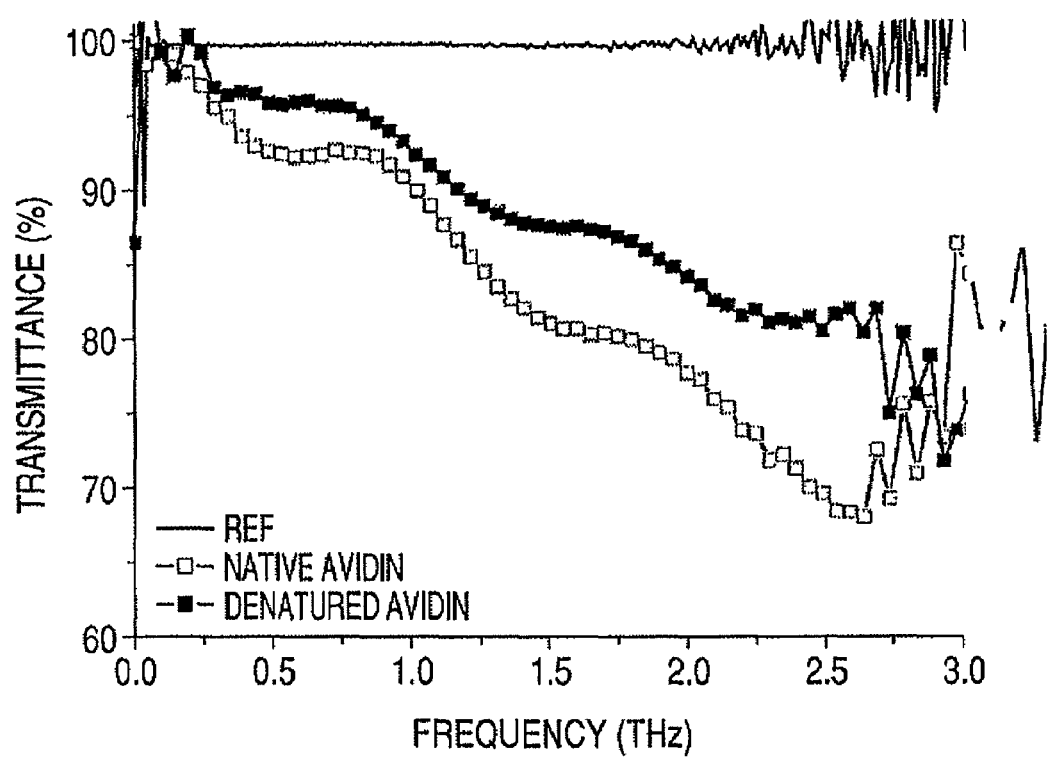
FIG. 5 is a graphic diagram illustrating an example of a transmission spectrum of protein (avidin).

A similar experiment was carried out with another kind of protein, avidin. The transmission spectrum of avidin when supplied at 20 mg/ml in 45 µl is illustrated in FIG. 5. The heat-denatured avidin (72° C. for 3 min.) (indicated by the black square, and the white square is one in normal state) shows an increase in transmittance just as in the case of BSA. However, the degree of the increase is different from that of the BSA. It is found that a ratio of a change in transmittance or phase shift amount due to the denaturation varies depending on the kind of the protein.

In this way, even when a significant characteristic vibration spectrum cannot be found in the THz wave region, if a rate of change in property of the protein to frequency, namely, a slope of change at a certain frequency change is obtained, the degree of protein denaturation can be detected.

Figure 6A:
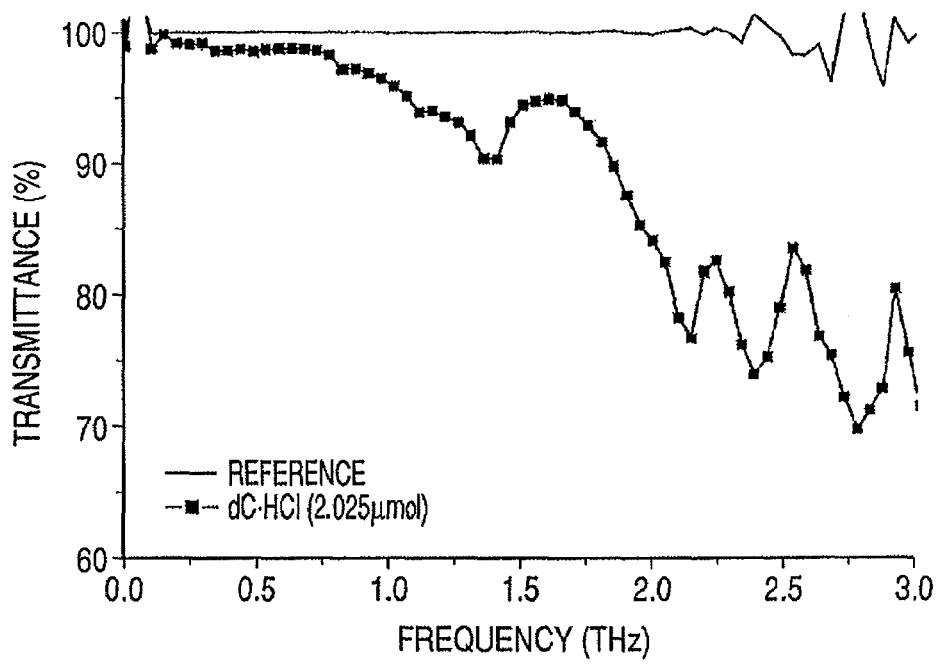
FIGS. 6A and 6B are graphic diagrams illustrating examples of a transmission spectrum and a phase shift spectrum of nucleobases (dC•HCl).
Figure 6B:
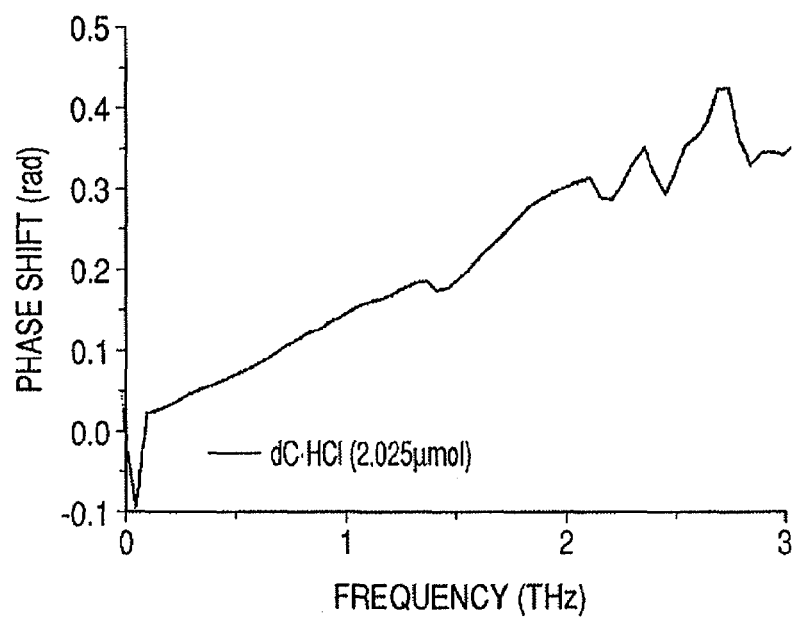

Here, the definition of the case where the characteristic vibration spectrum cannot be distinguished will be mentioned. As is already described with reference to FIG. 3B, when the characteristic vibration spectrum is absent, the phase shift spectrum only monotonically increases with respect to frequency. In contrast, in the case of deoxycytidine hydrochloride (dC•HCl) as a comparative example, a significant characteristic vibration spectrum is observed as illustrated in FIG. 6A. Further, as can be seen from the phase shift spectrum of FIG. 6B, a turning point, an inflexion point, and a discontinuity are present corresponding to the vibration peaks. In should be noted that, in this example, 0.2 THz or less would be a noise component and thus it was not used for the determination of a turning point, an inflexion point, and a discontinuity of the phase shift spectrum. In this way, the case in which characteristic vibration spectrum is not observed can be defined as one in which a turning point, an inflexion point, and a discontinuity are not found in a phase shift spectrum.

Example 2

A second example of the present invention is to apply the detection of the denatured state of protein like the one described in Example 1 to the diagnosis of disease.

The three-dimensional steric structure, or conformation, of protein is the most important for the activity of the protein. A slight change in conformation leads to a significant increase in binding with DNA or a ligand or binding between proteins. In this way, it may affect not only on the homeostasis of cells but also the survival of cells in some cases. Abnormal protein derived from an abnormal change in the conformation of protein, that is, the denaturing of protein, has already been reported with respect to various diseases such as cancers, mad cow disease, and dementia related to Alzheimer's disease and Parkinson's disease. In this case, proteins used as a target for some pathological diagnosis will be described.

The p53 gene has been known as a typical tumor suppresser gene. The p53 protein normally produced by this gene serves to suppress the development of cancer. The mutated p53 gene with DNA mutation, deletion, or the like may produce mutated p53 protein which loses normal functions. In other words, the mutated p53 protein loses the conformation of the normal p53 protein, and thus, it cannot have activity. Abnormalities of the p53 protein structure have been reported for almost half of the actual human cancers. It means that almost 100% of cancers may cause mutation in any part of the p53 pathway. The mutation makes it hard for cells to die from apoptosis. In the property diagnosis of cancer, the presence or absence of mutation (i.e., denaturation) of the p53 protein may be detected using a frequency spectrum with respect to the THz wave using the method of Example 1. Thus, it can be applied to the reactivity to a medical treatment or the selection of therapeutic procedures, and the speculation of clinical prognosis.

On the other hand, bovine spongiform encephalophathy (BSE) is the illness caused by accumulation of pathological protein "prion" in the brain. The abnormal prion entering into the human body for any reason is connected with normal the prion originally present in the living body, and in particular, with harmless protein which is abundantly present in neural cells. Thus, the cells are made abnormal one after another. The mutated prion becomes a lump and destroys the neuron, producing holes in the brain. One of the reasons which make the research difficult is that BSE is not applied to a classification of the common infectious diseases. In a typical infectious disease, bacteria, viruses, and the like enter the human body to form the focus in the body. At present, bacteria or viruses which cause the illness of BSE have not been found. In addition, medical treatment is also difficult because bacteria or viruses are not detected by the immune system, even if infected. The most leading means for diagnosing such a disease earlier is detection of denatured protein (the denatured prion) by the method of the present invention.

Further, malignant melanoma is one kind of skin cancer. With respect to the immunoreaction in which transition of fatal malignant melanoma is prevented and delayed, research has found that when a specific marker is on the surface of a patient's immune cell, a life-prolonging rate becomes high. It is observed that, if a patient's T-lymphocytes (immune cells for killing tumors) have specific protein called chemokine acceptor CXCR3, a patient's survival rate increases by about 50%. That is, an improvement in a survival rate is possible by induction of a specific chemokine acceptor in the T cell surface. It is effective to carry out the determination of the presence or absence of the protein and the amount of expression using the THz wave light in the method of Example 1.

It is reported that there are abnormalities of proteins which are common in nerve cells of patients of FTD in which the frontotemporal lobe shrinks, which is one of the observed types of dementia, and amyotrophic lateral sclerosis ("ALS"), in which the muscles gradually lose their ability to move. It is expected that abnormalities of proteins mentioned above may lead to development of a new cure. In addition, it attracts attention to relevance with other nerve incurable diseases such as the Alzheimer disease. It is known that protein "TDP-43" which exists in the nucleus of normal cell exists in out of the nucleus of brain cells of any patient of FTD and ALS, and the cell itself has stopped functioning normally. The detection method of the present invention is promising as a new diagnosing method if the denatured protein can be perceived as a change in conformation in comparison with a healthy person's normal protein.

The detection of abnormal proteins faces an urgent need as described above. Nevertheless, a detection method that is as easy to use and as exact as would be desired has not been available. Detection methods often used now include the ELISA method and the Western Blotting method, which have been mentioned in the description of the background, and also an immunity sedimentation method and the like. Any of such known methods gives due consideration of having a loss of the antigenicity of the detection-target protein by processing for detection, i.e., reduction, and heat-treatment. Further, detection methods for other abnormal proteins utilize the antigen-antibody immunities. In other words, a synthesized antibody is only employed to detect the difference of amino acid sequences of parts of the respective proteins. Even the antibody cannot detect a denaturation of a protein, and thus it is difficult to state positively that the protein is functioning normally. In addition, most of those methods require detection using a fluorescent dye at a final stage. However, the mechanism of binding between the fluorescent dye and DNA has not been clarified. That is, a question whether the detected protein actually reproduces the state of the protein in the living body remains. The most important is that the dynamic overall picture of protein itself cannot be grasped, although a difference in amino acid sequence, which is part of the protein, can be detected by any of those methods.

Then, a THz wave spectrum like the one mentioned in Example 1 can be advantageously used in a simple detection of the denaturation of abnormal protein without pre-treatment or addition of a fluorescent marker. All cases mentioned herein are only examples of pathological diagnosis. The inventive detection method is able to detect abnormalities or denaturation of proteins related to various illnesses and applicable to various pathological diagnoses.

Example 3

A detection method of a third example in accordance with the present invention is to be applied on the detection of DNA. Salmon DNA with an average base length of 2,000 bases was subjected to a measurement in a manner similar to that of Example 1. In general, DNA takes two different states, a ds-DNA state forming a double-stranded structure and a ss-DNA state forming a single-stranded structure as a result of unfastening the binding in double-stranded structure (thermal denaturation condition: 95° C. for 5 minutes). DNAs in those two states, each 10 mg/ml in 60 µl, were subjected to the measurement and the transmission spectra thereof obtained were then illustrated in FIG. 7.

Figure 7:
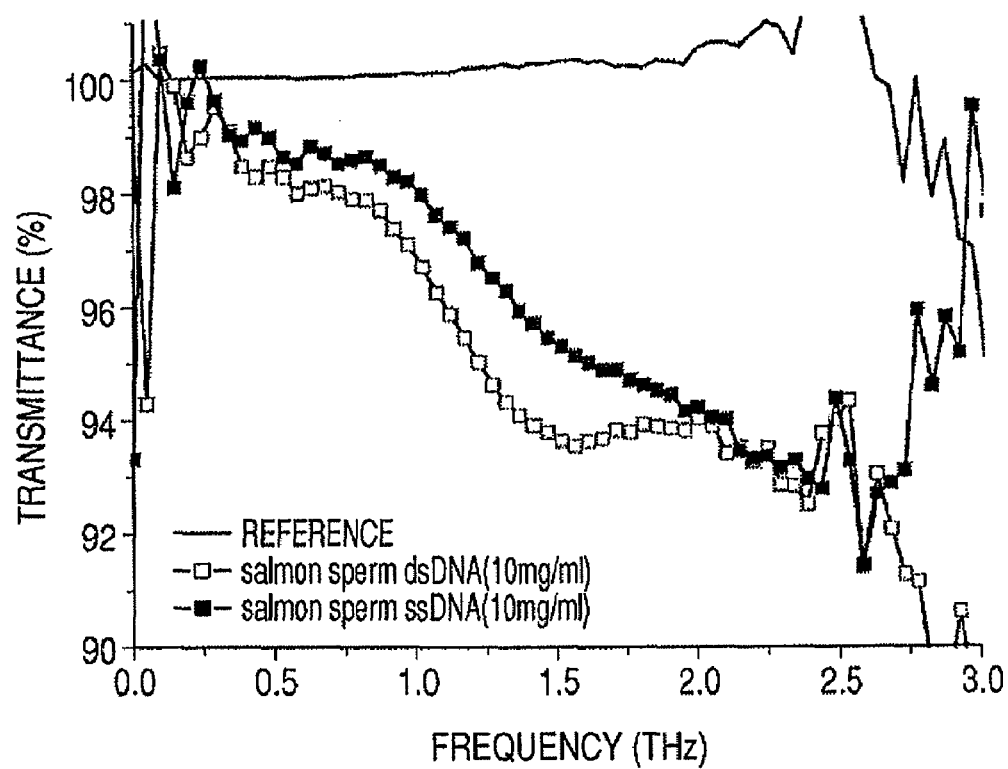
FIG. 7 is a graphic diagram illustrating an example of a transmission spectrum of DNA.

As is evident from FIG. 7, a remarkable difference is found in transmission spectra. The transmittance of the ss-DNA (represented by the black square) is higher than that of the ds-DNA. In other words, a ratio of average changes from 1 THz to 2 THz may be compared using the slope of a straight-line approximated by the least square method to detect a ratio of the ss-DNA and the ds-DNA in the sample.

Now, an example of using the detection method as for a DNA sensor will be described. A probe DNA for detecting the presence or absence of a certain base sequence is previously prepared. When a sample of DNA to be examined in single-stranded state is supplied and bound to the probe DNA to form a double strand, it means that the sample may express a target base sequence. In contrast, when the sample DNA remains in single-stranded state, it means that such a target base sequence is not present in the sample. Therefore, the transmission spectrum of the THz wave as described above can be used for determining the presence or absence of the expression.

This example provides a detection method and a detection apparatus with the ability of simply detecting a difference in the structure of DNA with a difference of the slope of the transmission spectrum. The transmission spectrum is the frequency spectrum characteristics of the THz wave. Although not shown here, the detection can be also attained using a phase shift spectrum, a time wavelength shift, or a combination thereof as described in Example 1.

Example 4

A fourth example in accordance with the present invention indicates that even a state change of an inorganic substance can be similarly detected with the shape of the frequency spectrum of the THz wave.

Figure 8:
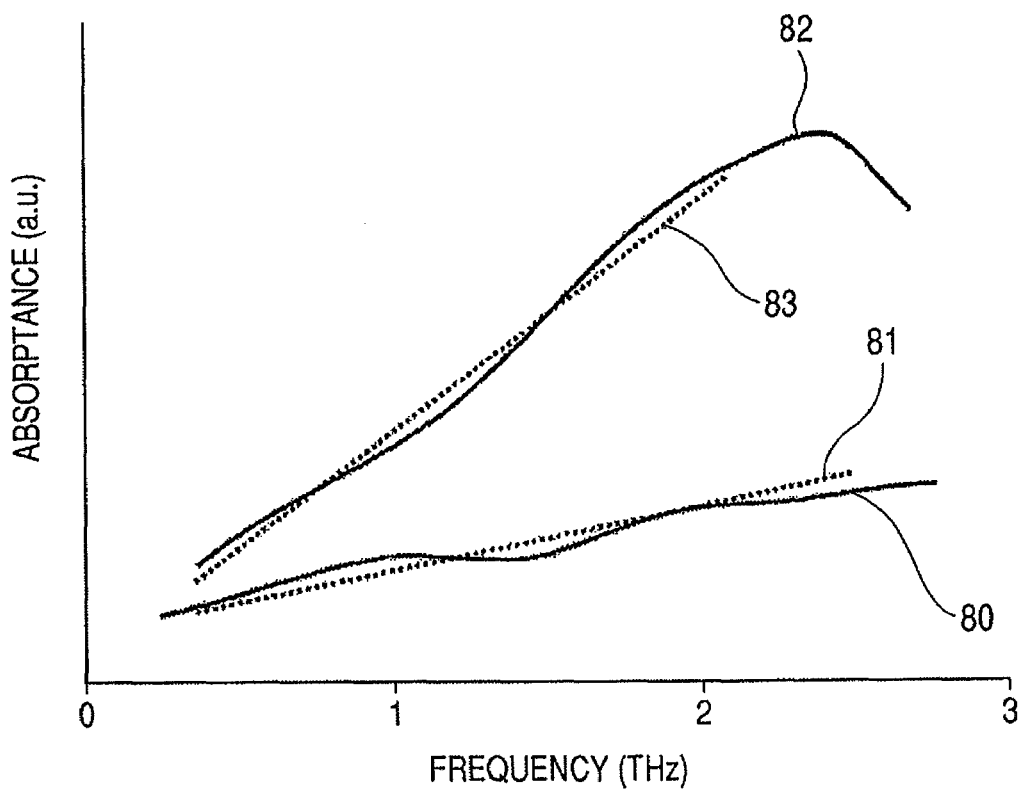
FIG. 8 is a graphic diagram illustrating an example of an absorption spectrum of an inorganic crystal (MgF).

FIG. 8 illustrates a difference in absorption spectrum with respect to the THz for an $MgF_2$ crystal as an important optical material in each of two cases: a non-doped case (solid line 80) and a Co-doped case (solid line 82). Each case shows almost monotone increasing from 0.5 THz to 2.5 THz. In contrast, one doped with Co shows a peak at the vicinity of 2.0 THz. In each case, when the slope of a straight-line approximated by the least square method, the dotted lines 81, 83 in FIG. 8 are obtained.

In this way, the Co-doping causes a significant difference between the slopes 81, 83. Thus, a difference in crystal structure with the doping can be detected as a function of doping concentration.

Such a fact means that the difference can be detected by the slope of the frequency spectrum in a manner similar to one described above even in the case of doping a different matter, introducing an impurity without intentional doping, or using a poor-quality crystal. In addition, the size of the crystal used is not particularly limited as far as it leads to a significant attenuation to the THz wave. Thus, the present detection method is applicable to the detection of a state change of any of $LiNbO_3$, crystalline quartz, sapphire, and the like. In addition, it is applicable not only to a solid crystal but also to a liquid crystal. Further, it is applicable to the detection of state changes of resin materials such as Teflon™, polyethylene, and polyolefin.

Example 5

A fifth example in accordance with the present invention does not employ the detection method in which a sample is allowed to interact with the THz wave in space as described in any of the aforementioned examples. The present example employs a transmission line apparatus such as one illustrated in FIG. 10.

Figure 10:
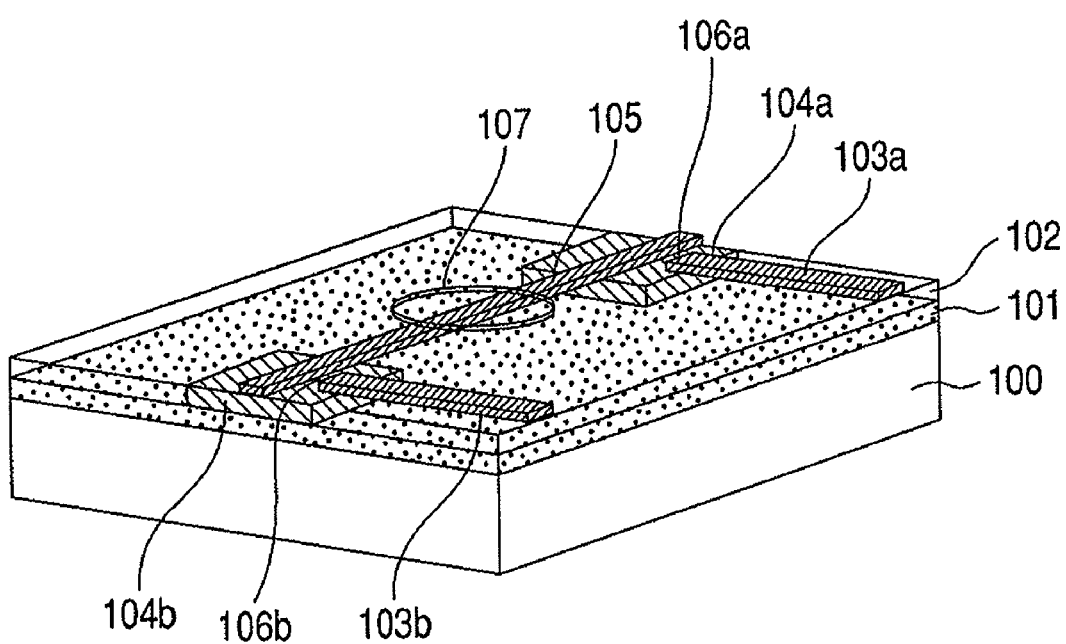
FIG. 10 is a perspective view of an embodiment using a transmission-line type sensor.

In FIG. 10, the reference numeral 100 is a holding substrate made of Si and the like, 101 is a ground plane made of metals such as Ti/Au, 102 is a dielectric material such as BCB (Cycroten™, manufactured by Dow Chemical Ltd.), and 105 is a transmission line made of a metal pattern of Ti/Au. In the present example, a microstrip line is used as a transmission line 105.

Further, the irradiation unit and the detection unit for the THz wave are accumulated. Both the detection unit and the irradiation unit include LT-GaAs thin films 104a, 104b, leading lines 103a, 103b, and electrode interval parts 106a, 106b. A THz wave can be generated by applying a voltage on the interval part 106b and irradiating with a femtosecond laser. A current component synchronized with irradiation of the femtosecond layer may be detected by the other interval part 106a.

A sample is applied to the upper part of the transmission line 105 as represented by the reference numeral 107. In this way, a difference in status of the sample 107 is detected by the THz-TDS system in a manner similar to Example 1 using shift amounts of a transmission spectrum, a phase shift spectrum, and a time wavelength. The detection is, just as in the case of FIG. 1, a lock-in amplifier 113 acquires a signal as a mixture of a THz wave signal being amplified by an amplifier 5 and a signal from an oscillator 9. Subsequently, an output from the lock-in amplifier 113 is processed in PC 114.

Figure 11:
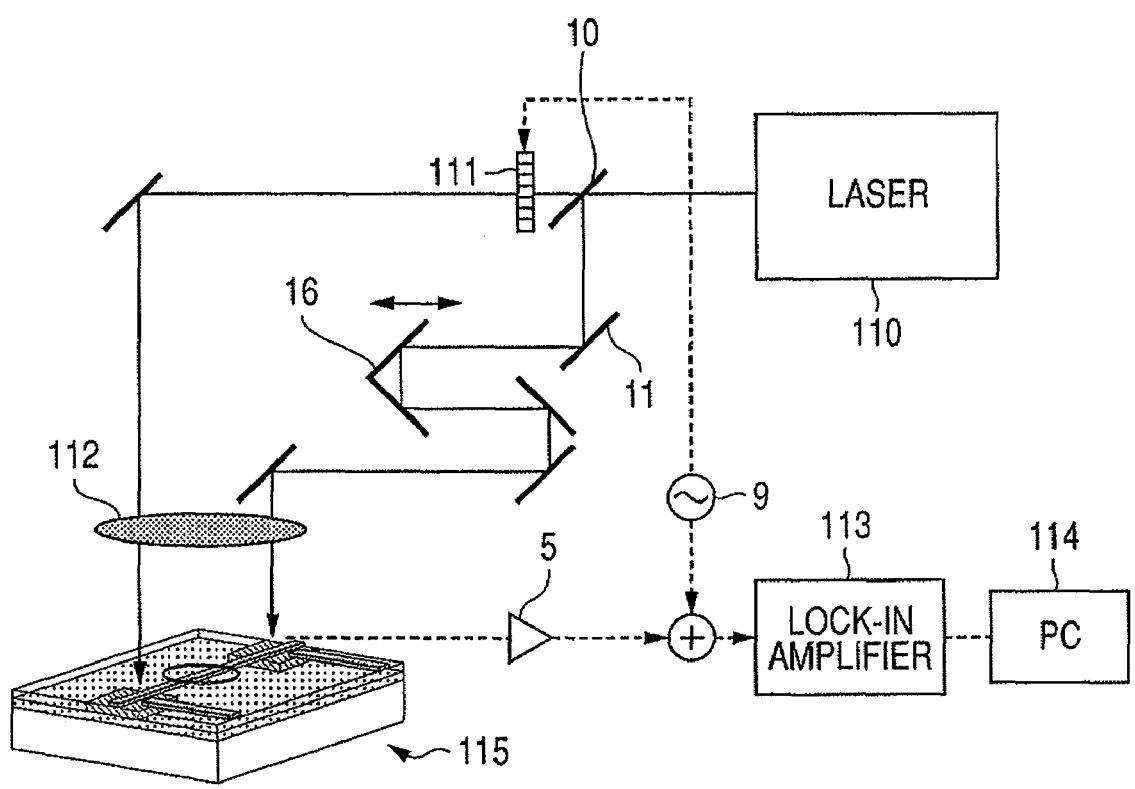
FIG. 11 is a diagram of an optical arrangement of a detection apparatus including the sensor of FIG. 10.

The THz-TDS system for evaluating the output is illustrated in FIG. 11. In this figure, the same reference numerals are allocated on the same functional portions as those in FIG. 1. Here, a lens 112 is used to adjust two laser beams from a laser 110 to be irradiated to the interval parts 106a, 106b of a transmission line device 115, respectively. Modulation on the side of electromagnetic-wave generation is carried out by using an optical chopper 111 driven by a signal from the oscillator 9 but not by a voltage applied on the device.

Figure 12A:
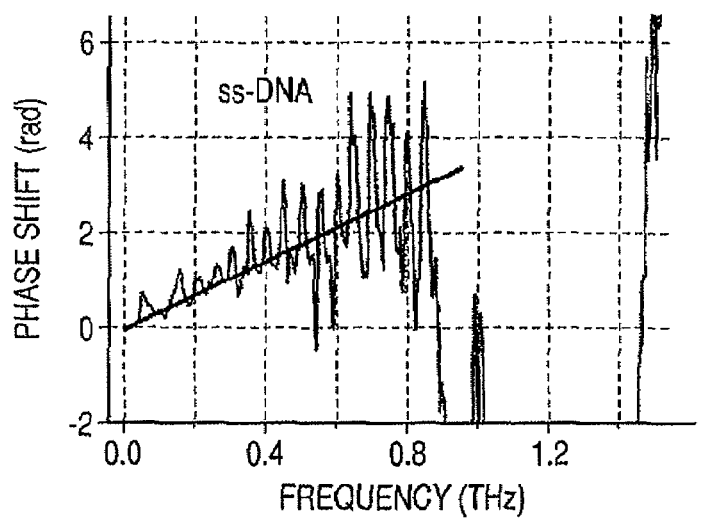
FIGS. 12A, 12B and 12C are graphic diagrams illustrating an example of a phase shift spectrum using a detection apparatus having a transmission-line type sensor.
Figure 12B:
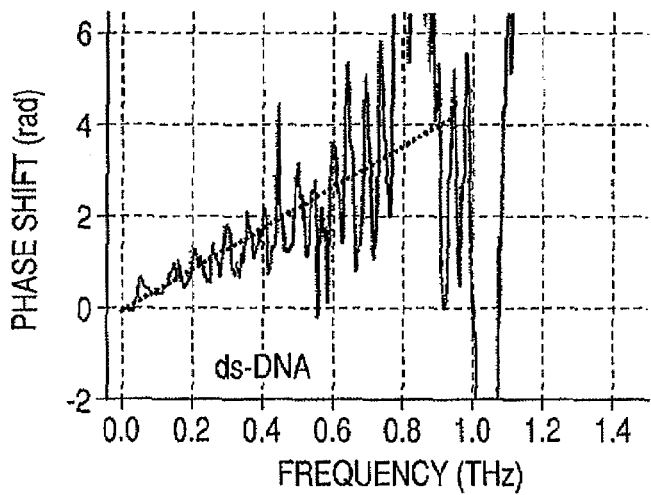

The sample 107 used was DNA as in the case of Example 3. FIGS. 12A and 12B illustrate examples of a phase shift spectrum obtained by application of 900 nl of DNA at a concentration of 0.5 µg/µl. FIG. 12A illustrates a result obtained from ss-DNA and FIG. 12B illustrates a result obtained from ds-DNA. For the calculation of data, a region where the sample and the electromagnetic wave actually interact with each other is estimated and the effect of the interaction on the applying amount is normalized.

As is evident from FIGS. 12A and 12B, the available band of the transmission line 105 used in the measurement is up to about 1 THz. The transmission line 105 may generate ripples as large and minute fluctuations of the frequency characteristics with an influence of reflection or the like. However, an average slope for the single strand is represented by the solid line in FIG. 12A and an average slope for the double strand is represented by the dotted line in FIG. 12B. Therefore, a difference between the slopes can be discriminated. Here, the transmission spectrum also includes a large noise component based on ripples. Thus, the phase shift spectrum, which can be more easily discriminated, has been used. Alternatively, however, a transmittance (i.e., transmission) spectrum or an absorption spectrum may be used.

Figure 12C:
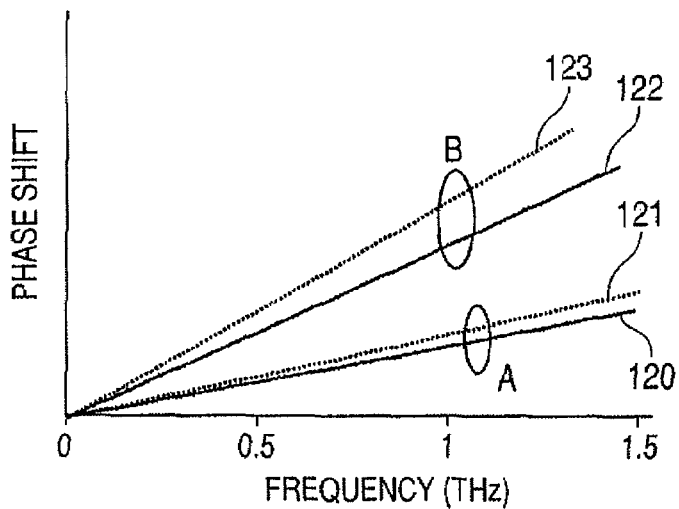

FIG. 12C apparently illustrates the appearance of the phase shift spectrum. Similarly, the solid line represents a single strand and the dotted line represents a double strand. The smaller amounts of the samples correspond to the lines 120, 121 (A). The larger amounts of the samples correspond to the lines 122, 123 (B). As is evident from the results of Example 3, the single strand shows higher transmittance. When the amount of the single strand is equal to the double strand, the former shows a smaller slope of the phase shift spectrum than that of the double strand. Further, the single strand and the double strand can be discriminated with respect to a ratio of change of the phase shift spectrum due to their supplying amounts. Such discrimination may be also attained with a rate of change in peak shift amount or peak amount of the time waveform as described in Example 1 (see FIG. 3A).

The present example has a merit in that the application of a sample on the vicinity of the transmission line allows the sample to be detected even if a minute amount of the sample is applied.

Example 6

Figure 13A:
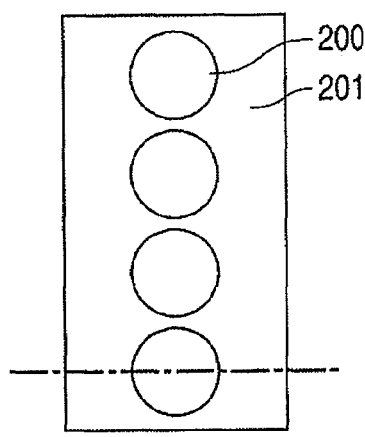
FIGS. 13A, 13B and 13C are block diagrams illustrating a reflection-measurement type detection apparatus in accordance with another embodiment of the present invention.
Figure 13B:
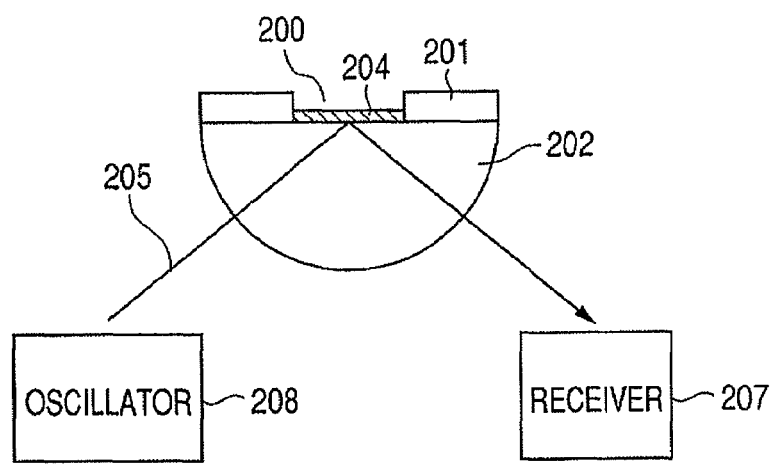
Figure 13C:
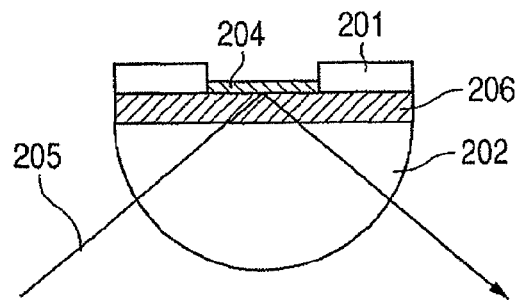

A sixth example of the present invention will be described with reference to FIGS. 13A to 13C. In this example, an evanescent wave is used together with the use of a total reflecting prism coupler 202, thereby improving the sensitivity to the change with a reflection wave. FIG. 13A is a plan view of the prism coupler and FIG. 13B is a cross sectional view along the dashed line of FIG. 13A. In FIGS. 13A to 13C, the reference numeral 201 is a partition-forming member attached on the upper surface of the prism coupler 202 in semi-cylindrical shape. The member 201 is provided with a plurality of wells 200. The prism coupler 202 is preferably a prism made of a high-resistance Si material because of its small loss and dispersion of THz waves. Alternatively, however, the material may be one of a dielectric material such as magnesium oxide, and a resin material such as Teflon™.

In the above configuration of the detection apparatus, as shown in FIG. 13B, a THz wave 205 is incident on the coupler 202 and then reflected THz wave is then output of the coupler 202. In this case, an evanescent wave is generated in the vicinity of the reflective surface. Thus, a membrane filter 204 is placed on a well 200, followed by supplying a sample. Consequently, a high-sensitivity measurement can be attained as a result of an interaction between the evanescent wave and the sample. In this case, for example, the reflected THz wave sensitively reflecting the state of the sample is detected at the respective frequencies. The results of the detection are then plotted as the reflectance values at a plurality of frequencies. Consequently, a reflective spectrum can be obtained. Further, the above slope of the straight line can be calculated from such a reflective spectrum.

The partition-forming member 201 is one on which wells 200 are arranged as illustrated in FIG. 13A to allow a plurality of samples to be assayed at a high speed. Here, for allowing the sample to effectively interact with an evanescent wave, the thickness of the membrane filter 204 is preferably about 50 μm. The membrane filter 204 may be not always used for the sample. For instance, a liquid cell may be placed. Alternatively, any of powders and solids may be directly placed on wells 200.

Here, an overall measurement system for acquiring the data base of calibration curves may be the same one as that of Example 1 as illustrated in FIG. 1. When a sample is actually subjected to the detection, both a detector 207 for detecting a reflected wave and an oscillator 208 for oscillating a single frequency may be placed as illustrated in FIG. 13B. For investigating the slope of a straight line in the frequency spectrum, a plurality of single-frequency oscillators may be prepared. In FIG. 13B, one ray path is illustrated. Alternatively, a structure for multiple-reflection on the sample holding section may be employed.

Further, a method having a higher efficiency than one using total reflection with an evanescent wave is, as shown in FIG. 13C, of a type of placing a conductive material 206 between the membrane filter 204 and the surface of the coupler 202. The conductive material 206 is preferably one deposited with an n-type Si thin film (2.5 μm in thickness). Surface plasmons may be generated at a frequency of about 3 THz. Alternatively, the conductive material 206 may be any of other semiconductors such as InAs and GaAs, doped with impurities and metals, such as Au and Al.

The membrane filter 204 with a thickness of about 50 μm is arranged on the surface of the conductive material 206 as described above to sensitively reflect the state of a sample. In this case, an angle at which a dip with a strong absorption of a reflected THz wave occurs is present. Thus, the reflected THz waves at the respective frequencies are detected at this angle. The results of the detection are plotted as reflectance values at the respective frequencies, thereby obtaining a reflective spectrum. Then, the above slope of the straight line can be calculated from the reflective spectrum. Therefore, such a measurement allows the state of a sample to be evaluated with sufficient sensitivity. This example is of a so-called Kretschmann configuration where the conductive material 206 is placed between the sample and the total reflection surface. Alternatively, a so-called Otto configuration (not shown) where a membrane filter with a sample is placed between the total reflection surface and the conductive material may be used. In this case, the thickness of the conductive material is unlimited. If the measurement is performed at 1 THz, the interval in which the membrane filter is placed is preferably about 10 μm or less. In this case, the structure may also be of multiple reflections.

This example provides a measurement system in which a small amount of a liquid sample may be placed in a liquid cell and the liquid may be more sensitively detected. In this case, the detection method may be the same as that of any of Examples 1 to 3.

Example 7

In a seventh example in accordance with the present invention, a difference between the solid (crystal) state of a bio-related molecule and the state of a dissolved product is discriminated. In this case, the dissolved product is prepared by dissolving the bio-related molecule in an aqueous solution and applying the solution on a micromembrane filter, followed by being dried.

Figure 15:
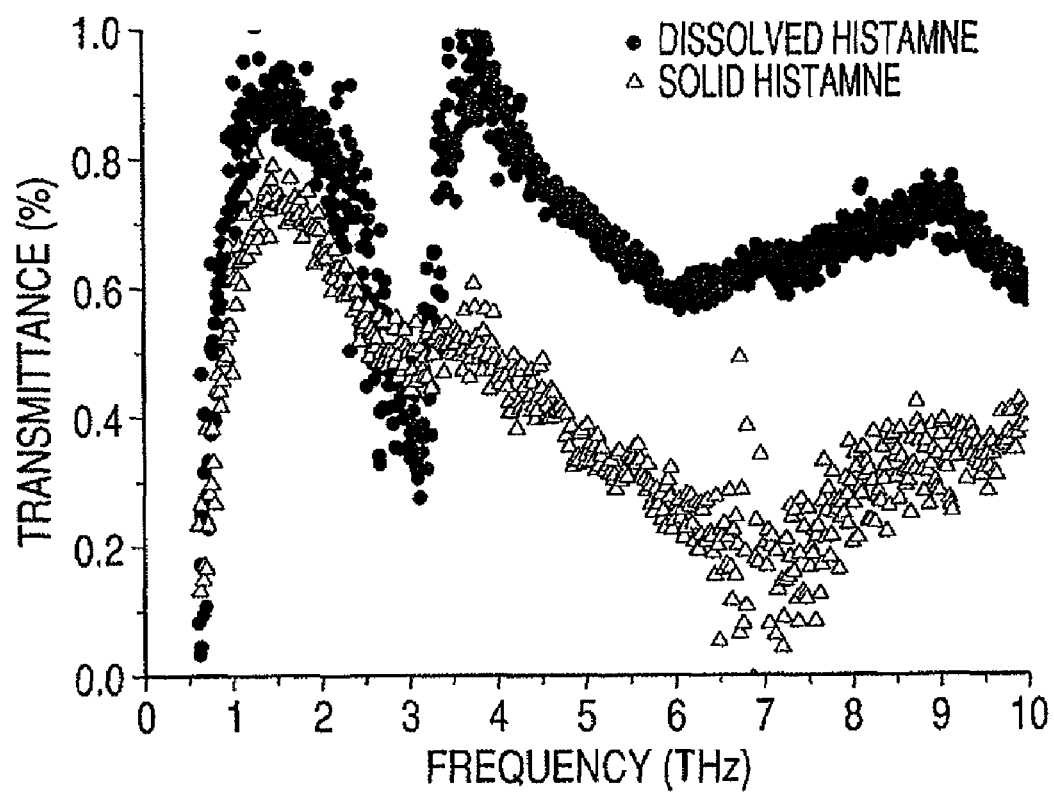
FIG. 15 is a graphic diagram illustrating another measurement example of a transmission spectrum of hormone.
Figure 16:
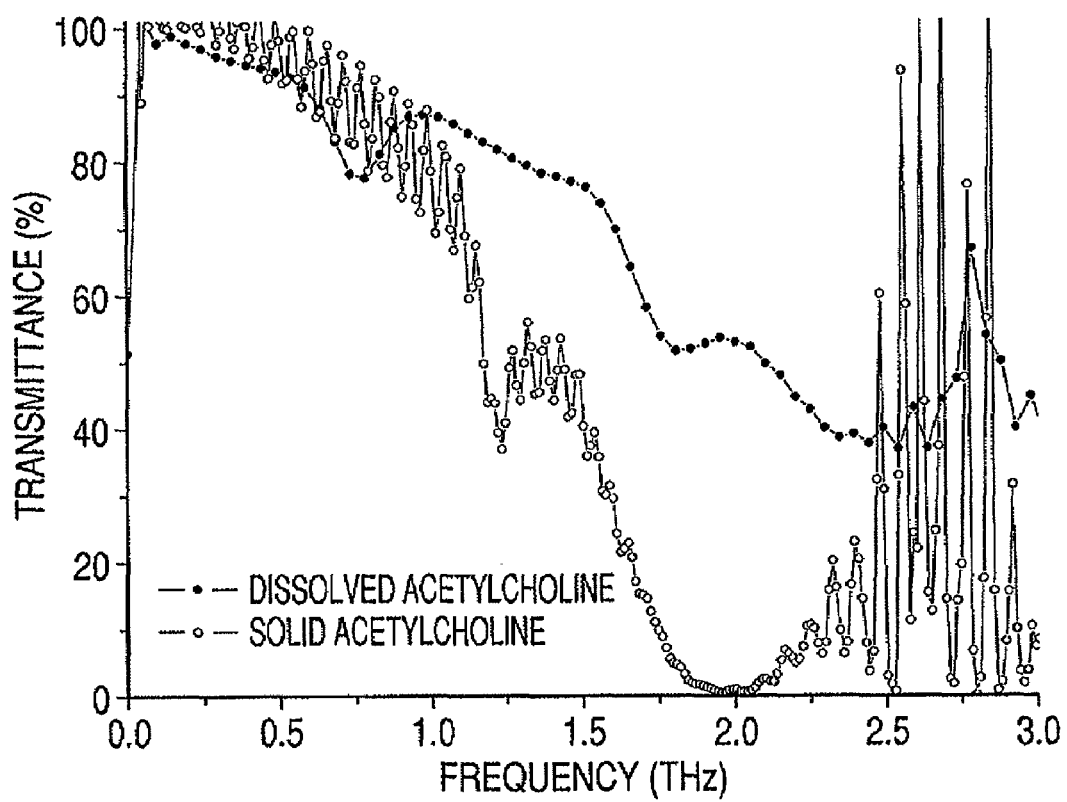
FIG. 16 is a graphic diagram illustrating another measurement example of a transmission spectrum of neurotransmitter.

FIG. 15 illustrates transmission spectra of hormone (one of bioactive substances) such as histamine ($C_5H_9N_3$, MW: 111.15) in solid state (solid) and dissolved state (dissolve), which were measured with the FT-IR apparatus, respectively. FIG. 16 illustrates the results of the measurement with THz-TDS performed on a bioactive substance (neurotransmitter) such as acetylcholine ($(CH_3)_3N^+CH_2CH_2OCOCH_3Cl^-$; MW: 181.66) in solid state (solid) and dissolved state (dissolve), respectively. The dissolved product was adjusted to a solution concentration of 20 mg/ml and a dropping amount of 30 μl. The solid was mixed with polyethylene powder and formed in pellet. Subsequently, both of them were subjected to the measurement.

For example, histamine can be discriminated because the slope of the dissolved product is higher than that of the solid with respect to the slope of a straight line at 1.5 to 3 THz. On the other hand, acetylcholine can be discriminated because the slope of the solid is higher than that of the dissolved product with respect to the slope of a straight line at 0.5 to 2 THz. The sample is present in crystal state in the solid. However, the crystallinity of the sample becomes worse in the dissolved product and turns into a state containing a hydrate. Therefore, it may be represented by a difference in transmission spectrum of THz. According to the present invention, a state difference can be evaluated by the slope of a straight line approximated at a selected frequency within the range of the transmission spectrum.

According to this example, the present invention may be entirely applied to a biomolecule (bioactive substance) responsible for vital activity and provided as a disease marker to carry out a state examination. The biomolecule may be any of other hormones and a neurotransmitter.

Example 8

An eighth example in accordance with the present invention is applied to a food additive, and a discrimination is made between solid and a dissolved product as in the manner in Example 7.

Figure 17:
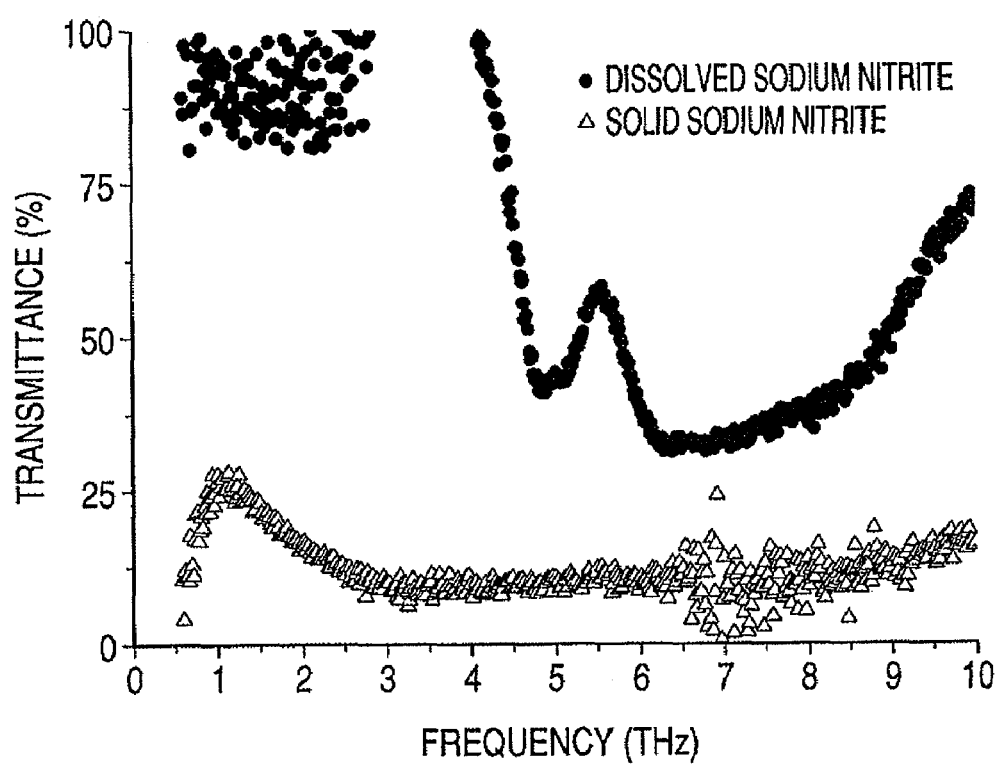
FIG. 17 is a graphic diagram illustrating another measurement example of a transmission spectrum of a food additive.

FIG. 17 illustrates an example in which sodium nitrite ($NaNO_2$; MW 69) was measured using the FT-IR apparatus. A dissolved product was adjusted to a solution concentration of 20 mg/ml and a dropping amount of 30 μl.

For instance, a discrimination can be made between solid and a dissolved product with the slope at 4 to 5 THz.

According to this example, various kinds of food additives can be examined in added state in a nondestructive manner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-327801, filed Dec. 5, 2006, which is hereby incorporated by reference herein in its entirety.

What is claimed is:

1. A method of detecting a state change of a substance using an electromagnetic wave selected from a frequency range of 0.1 THz to 10 THz, comprising:
   a first step of placing a substance on a sample holding section;
   a second step of irradiating the substance with the electromagnetic wave;

a third step of detecting an electromagnetic wave that has passed through or been reflected from the substance;

a fourth step of determining a frequency dependence of a property of the substance with respect to the irradiating electromagnetic wave from information about the detected electromagnetic wave and the irradiating electromagnetic wave and then calculating a slope of a straight line or a slope of a straight line obtained by straight-line approximation of the frequency dependence of the property of the substance; and a fifth step of evaluating a degree of state change from a standard state of the substance by comparing a previously-obtained slope of a straight line of the frequency dependence of the property of the substance in the standard state and the slope of the straight line of the substance calculated in the fourth step.

2. A detection method according to claim 1, wherein the property of the substance is at least one selected from a transmittance, an absorbance, a reflectance, and a phase shift.

3. A detection method according to claim 1, wherein the frequency range used for determining the slope of the straight line of the frequency dependence of the property of the substance is selected from a range of 0.2 THz to 2.5 THz.

4. A detection method according to claim 1, wherein the substance is a bio-related molecule.

5. A detection method according to claim 1, wherein the substance is a food additive, the method further comprising a step of carrying out a state examination.

6. A detection method according to claim 4, wherein the bio-related molecule is a protein selected from P53 protein, TDP-43 protein, and prion protein, the method further comprising a step of carrying out a pathological diagnosis by detecting the state change of the bio-related molecule.

7. A detection method according to claim 4, wherein the bio-related molecule is a bioactive substance selected from hormones and neurotransmitters, the method further comprising a step of carrying out a state diagnosis of the bio-related molecule.

8. A detection method according to claim 1, wherein:

the substance is a liquid substance; and a micromembrane filter is used in the sample holding section, and the method further comprising a step of correcting the frequency dependence by removing a wave undulation occurring in the frequency dependence due to an interference of the irradiating electromagnetic wave at two end surfaces of the micromembrane filter.

9. A detection method according to claim 1, wherein the frequency dependence of the property of the substance with respect to the irradiating electromagnetic wave is determined using a high-frequency transmission line having the sample holding section.

10. A detection method according to claim 1, wherein the frequency dependence of the property of the substance with respect to the irradiating electromagnetic wave is determined using a total reflecting prism having the sample holding section.

11. A detection method according to claim 1, wherein a corresponding relation between the degree of state change from the standard state of the liquid substance and the slope of the straight line is obtained in advance and the degree of state change is evaluated by using the corresponding relation.

12. A detection apparatus for detecting a state change of a substance using an electromagnetic wave selected from a frequency range of 0.1 THz to 10 THz, comprising:

a sample holding section for holding a liquid substance, the sample holding section being formed of a micromembrane filter;

an irradiation means for irradiating the liquid substance held in the sample holding section with the electromagnetic wave;

a detection means for detecting an electromagnetic wave that has passed through or been reflected from the liquid substance;

a frequency dependence determination means for determining a frequency dependence of a property of the liquid substance with respect to the irradiating electromagnetic wave from information about the detected electromagnetic wave and the irradiating electromagnetic wave;

a correction means for correcting the frequency dependence by removing a wave undulation occurring in the frequency dependence due to an interference of the irradiating electromagnetic wave at two end surfaces of the micromembrane filter;

a calculation means for calculating a slope of a straight line or a slope of a straight line obtained by straight-line approximation of the frequency dependence of the property of the liquid substance that has been corrected by the correction means; and an evaluation means for evaluating the state change of the liquid substance by comparing a previously-obtained slope of a straight line of the frequency dependence of the property of the liquid substance in a standard state and the slope of the straight line of the liquid substance calculated by the calculation means.

* * * * *